(12) United States Patent
Hu (10) Patent No.: US 11,815,464 B2
(45) Date of Patent: *Nov. 14, 2023

(54) COLORIMETRIC CHEMICAL SENSOR WITH ENHANCED COLOR SENSITIVITY

(71) Applicant: DrinkSavvy, Inc., Brooklyn, NY (US)

(72) Inventor: Min Hu, Brooklyn, NY (US)

(73) Assignee: DrinkSavvy, Inc., Brooklyn, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/868,604

(22) Filed: Jul. 19, 2022

(65) Prior Publication Data

US 2023/0003656 A1 Jan. 5, 2023

Related U.S. Application Data

(63) Continuation of application No. 16/381,436, filed on Apr. 11, 2019, now Pat. No. 11,415,522, which is a
(Continued)

(51) Int. Cl.
*G01N 21/78* (2006.01)
*G01N 33/14* (2006.01)
(Continued)

(52) U.S. Cl.
CPC .............. *G01N 21/78* (2013.01); *B82Y 20/00* (2013.01); *G01N 31/22* (2013.01); *G01N 33/14* (2013.01);
(Continued)

(58) Field of Classification Search
CPC ........ G01N 21/78; G01N 31/22; G01N 33/14; G01N 2021/7756; G01N 2600/00; B82Y 20/00
See application file for complete search history.

(56) References Cited

U.S. PATENT DOCUMENTS

| | | | |
|---|---|---|---|
| 11,415,522 B2 * | 8/2022 | Hu | G01N 31/22 |
| 2012/0293802 A1 * | 11/2012 | Ozin | G01N 21/45 356/402 |

(Continued)

OTHER PUBLICATIONS

Yue, Y. et al. "Tunable one-dimensional photonic crystals from soft materials," Journal of Photochemistry and Photobiology C: Photochemistry Reviews 23 (2015) 45-67. Available online May 5, 2015 (Year: 2015).*

(Continued)

*Primary Examiner* — Jennifer Wecker
*Assistant Examiner* — Michelle Adams
(74) *Attorney, Agent, or Firm* — Michael T. Abramson; Jordan IP Law, LLC (57) ABSTRACT

A colorimetric sensor for detecting an analyte of interest in a fluid sample includes a lamellar photonic material having alternating layers of a first polymer layer and a second polymer layer. Each first polymer layer can be a molecularly imprinted polymer defining a cavity shaped to receive an analyte of interest. The photonic material is configured such that, when an analyte contacts the photonic material and becomes disposed within a cavity of the molecularly imprinted polymer, a refractive property of the photonic material changes, causing a detectable color change in the sensor.

30 Claims, 7 Drawing Sheets

Related U.S. Application Data continuation of application No. PCT/US2017/056553, filed on Oct. 13, 2017.

(60) Provisional application No. 62/407,765, filed on Oct. 13, 2016.

(51) Int. Cl.
  *G01N 31/22* (2006.01)
  *B82Y 20/00* (2011.01)
  *G01N 21/77* (2006.01)

(52) U.S. Cl.
  CPC . *G01N 2021/7756* (2013.01); *G01N 2600/00* (2013.01)

(56) References Cited

U.S. PATENT DOCUMENTS

| | | | |
|---|---|---|---|
| 2012/0309047 A1* | 12/2012 | Kofinas | G01N 21/78 436/95 |
| 2014/0106468 A1* | 4/2014 | Boersma | G01N 21/7743 422/69 |
| 2015/0104861 A1* | 4/2015 | Abramson | A47G 21/182 422/402 |
| 2019/0265169 A1* | 8/2019 | Hu | G01N 33/54373 |

OTHER PUBLICATIONS

Sekowski, J. et al. "Biotic-abiotic interfaces within a nanostructured polymer matrix platform: towards a completely abiotic system," ECBC FY10 ILIR Technical Report Executive Review (2010): 19, 6 pages (Year: 2010).*

Sellergren, B. et al. "Layer-by-Layer Grafting of Molecularly Imprinted Polymers via Iniferter Modified Supports," Adv. Mater. 14, 17 (2002) 1204-1208. (Year: 2002).*

Burgess, I.B. et al. "Structural colour in colourimetric sensors and indicators," J. Mater. Chem. C, 2013, 1, 6075-6086 (Year: 2013).*

Nicolas, H. et al. "Cucurbit[8]uril as Nanocontainer in a Polyelectrolyte Multilayer Film: A Quantitative and Kinetic Study of Guest Uptake," Langmuir 2015, 31, 10734-10742. Published: Sep. 15, 2015 (Year: 2015).*

* cited by examiner

COLORIMETRIC CHEMICAL SENSOR WITH ENHANCED COLOR SENSITIVITY

CROSS-REFERENCE TO RELATED APPLICATION

This application is a continuation of, claims priority to and the benefit of, and incorporates by reference herein in its entirety U.S. Nonprovisional patent application Ser. No. 16/381,436, which was filed on Apr. 11, 2019 and which claims priority to and the benefit of International Patent Application No. PCT/US2017/056553, which was filed on Oct. 13, 2017 and which claims priority to and the benefit of U.S. Provisional Patent Application No. 62/407,765, which was filed on Oct. 13, 2016 and the content of which is also incorporated by reference herein in its entirety.

TECHNICAL FIELD

In various embodiments, the present invention relates to a chemical sensor for use in detecting the presence of a target analyte in a fluid sample and, more specifically, to a colorimetric chemical sensor having alternating polymer layers for use in detecting a target analyte, for example, a date rape drug, in a fluid sample.

BACKGROUND OF THE INVENTION

The use of agents to incapacitate an individual has become more prevalent. Examples of such agents include gamma-butyrolactone (GBL), gamma-hydroxybutyrate (GHB), ketamine, Rohypnol, and the like. For example, the agents may be secretly placed in the beverage, such as an alcoholic beverage, of the intended consumer. Because these and similar agents are colorless, substantially odorless, and hard to detect, methods and devices are needed to detect the presence of such agents prior to consumption.

Although there are various techniques for detecting the presence of a chemical substance in a subject after the subject has consumed such an agent (e.g., by urinalysis using liquid chromatography-tandem mass spectrometry), such techniques are reactive in nature and merely confirm what may already be suspected, rather than proactive to detect the agent before it has been consumed. Furthermore, such techniques require expensive equipment run by highly trained technicians. Proactive testing devices may require exposing a portion of the liquid to be tested to a chemical reagent composition, which may result in a color change that indicates the presence of the agent in the liquid sample. Unfortunately, such tests are time consuming and may not be discrete.

Additional testing apparatus are available. For example, a subject may use drug testing strips that are hidden in or incorporated into, for example, a match, a match book, a cocktail napkin, a coaster, a placemat, a menu, and so forth. Although such techniques may appear more discreet, the subject may nevertheless be placed in an awkward position by having to perform the test. Moreover, the subject may have to carry out tests periodically over the course of a social encounter.

U.S. Pat. No. 9,285,352 describes an apparatus for testing a liquid using a straw, a stirrer, and/or a beverage container, where an indicator adapted to provide a visible reaction, e.g., a color change, upon exposure to an agent of interest may be adhered or otherwise bonded to a portion of the straw, stirrer, and/or beverage container. In particular, the indicator may cause the straw, stirrer, and/or beverage container, or the liquid contacting the straw, stirrer, and/or beverage container, to change color and/or fluoresce when an agent of interest is detected at or above a certain concentration.

Despite the advances made to date, there still exists a need for improved devices (e.g., colorimetric sensors) and methods for detecting chemical substances of interest in a liquid sample.

SUMMARY OF THE INVENTION

The invention is based, in part, upon the discovery of a new colorimetric sensor that can detect an analyte of interest in a fluid or liquid sample and that, in some implementations, may be disposed upon or integrated within a surface of a fluid receptacle (e.g., a glass or a cup) or a straw.

In one aspect, the colorimetric sensor includes a lamellar photonic material (e.g., a photonic gel or a photonic crystal) having alternating layers of a first polymer layer (e.g., a binding or receptor-containing polymer) and a second polymer layer (e.g., polystyrene). Each first polymer layer may be a molecularly imprinted polymer defining a cavity shaped to receive an analyte of interest. The photonic material may be configured such that, when an analyte contacts the photonic material and becomes disposed within a cavity of the molecularly imprinted polymer (i.e., the first polymer layer), a refractive property of the photonic material changes, causing a detectable color change in the sensor. The first polymer layer that is molecularly imprinted may contain a chromophore-containing polymer such as poly(urea-naphthalimide), poly(thiourea-naphthalimide), poly(styrene-urea-naphthalimide) or poly(styrene-thiourea-naphthalimide).

In certain applications, each first polymer layer is adapted such that, when the cavity receives the analyte of interest, the first polymer layer changes volume relative to a second polymer layer, thereby changing the refractive property of the photonic material. In some implementations, each first polymer layer further includes a chromophore indicator (e.g., a naphthalimide moiety) such that, when the cavity receives the analyte of interest, the analyte causes an electronically induced color change of the chromophore indicator that amplifies the color change in the sensor. In some variations, the chromophore indicator is incorporated into the first polymer layer as a co-polymer.

In certain embodiments, the alternating layers of the first and second polymer layers have a periodic distribution. In the absence of the analyte of interest, the periodic distribution may be from about 1 nm to about 1000 nm, or from about 100 nm to about 950 nm, or from about 200 nm to about 900 nm, or from about 300 nm to about 850 nm, or from about 400 nm to about 800 nm. In some embodiments, the periodic distribution in the presence of the analyte may be different from the periodic distribution in the absence of the analyte.

In a second aspect, the invention provides a method for detecting an analyte of interest in a fluid sample, which includes contacting a colorimetric sensor of the invention with a fluid sample to be interrogated and detecting whether a color change occurs when the sensor is contacted with the fluid sample. A color change being indicative that the analyte is present in the fluid sample. In certain embodiments, the colorimetric sensor includes a lamellar photonic material (e.g., a photonic gel or a photonic crystal) having alternating layers of a first polymer layer and a second polymer layer as described herein. Advantageously, in some implementations, the photonic material is configured so that, when an analyte contacts the photonic material and becomes disposed within a cavity of the molecularly imprinted polymer, a refractive property of the photonic material changes, causing a detectable color change in the sensor.

In certain embodiments, each first polymer layer is adapted such that, when the cavity receives the analyte of interest, the first polymer layer changes volume relative to a second polymer layer, thereby changing the refractive property of the photonic material. In certain embodiments, each first polymer layer further includes a chromophore indicator (e.g., a naphthalimide-containing moiety) such that, when the cavity receives the analyte of interest, the analyte causes an electronically induced color change of the chromophore indicator that amplifies the color change in the sensor. In some variations, the chromophore indicator is incorporated into the first polymer layer as a co-polymer.

In certain embodiments, the alternating layers of the first and second polymer layers have a periodic distribution. In the absence of the analyte of interest, the periodic distribution may be from about 1 nm to about 1000 nm, or from about 100 nm to about 950 nm, or from about 200 nm to about 900 nm, or from about 300 nm to about 850 nm, or from about 400 nm to about 800 nm. In some implementations, the periodic distribution in the presence of the analyte may be different from the periodic distribution in the absence of the analyte.

In another aspect, the invention provides a method of manufacturing a colorimetric sensor capable of detecting an analyte of interest in a fluid sample. In some embodiments, the method includes creating a first set of spaced apart layers of a first polymer. Each layer of the first set of spaced apart layers of the first polymer can be a molecularly imprinted polymer that defines a cavity shaped to receive an analyte of interest. The method may also include imprinting (e.g., using a stamp and/or a mold) the first set of layers into a coating that is or includes a second polymer (e.g., polystyrene), thereby creating a photonic material having alternating layers of first and second polymers configured such that, when an analyte contacts the photonic material and becomes disposed within a cavity of the molecularly imprinted polymer, a refractive property of the photonic material changes thereby to cause a detectable color change in the sensor.

In certain embodiments, the coating that is or includes the second polymer is disposed upon the surface of a substrate, e.g., a fluid receptacle (e.g., a cup, a glass, or the like) or a straw. In certain embodiments, the first set of spaced apart layers is disposed upon a release medium with anti-adhesive properties, e.g., a hydrophobic monolayer molecular coating such as a fluorinated self-assembled monolayer, a fluorinated diamond-like carbon coating, or the like.

BRIEF DESCRIPTION OF THE DRAWINGS

In the drawings, like reference characters generally refer to the same parts throughout the different views. For the purposes of clarity, not every component may be labeled in every drawing. Also, the drawings are not necessarily to scale, emphasis instead generally being placed upon illustrating the principles of the invention. In the following description, various embodiments of the present invention are described with reference to the following drawings, in which.

DETAILED DESCRIPTION

To provide an overall understanding of the invention, certain illustrative embodiments will now be described, including devices (e.g., colorimetric sensors), methods of making the devices, and methods of detecting an analyte of interest in a fluid sample. However, the devices and methods described herein may be adapted and modified as appropriate for the application being addressed and that the devices and methods described herein may be employed in other suitable applications. All such adaptations and modifications are to be considered within the scope of the invention.

Throughout the description, where compositions and devices such as a sensor are described as having, including, or comprising specific components, or where processes and methods are described as having, including, or comprising specific steps, it is contemplated that, additionally, there are compositions and devices of the present disclosure that consist essentially of, or consist of, the recited components, and that there are processes and methods according to the present disclosure that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a device or a method described herein can be combined in a variety of ways without departing from the spirit and scope of the present disclosure, whether explicit or implicit herein. For example, where reference is made to a particular feature, that feature can be used in various embodiments of devices of the present disclosure and/or in methods of the present disclosure, unless otherwise understood from the context. In other words, within this application, embodiments have been described and depicted in a way that enables a clear and concise application to be written and drawn, but it is intended and will be appreciated that embodiments can be variously combined or separated without parting from the present teachings and disclosure(s). For example, it will be appreciated that all features described and depicted herein can be applicable to all aspects of the disclosure(s) described and depicted herein.

The articles "a" and "an" are used in this disclosure to refer to one or more than one (i.e., to at least one) of the grammatical object of the article, unless the context is inappropriate. By way of example, "an element" means one element or more than one element.

The term "and/or" is used in this disclosure to mean either "and" or "or" unless indicated otherwise.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present disclosure also includes the specific quantitative value itself, unless specifically stated otherwise. As used herein, the term "about" refers to a ±10% variation from the nominal value unless otherwise indicated or inferred.

Where a percentage is provided with respect to an amount of a component or material in a composition such as a polymer, the percentage should be understood to be a percentage based on weight, unless otherwise stated or understood from the context.

Where a molecular weight is provided and not an absolute value, for example, of a polymer, then the molecular weight should be understood to be an average molecule weight, unless otherwise stated or understood from the context.

It should be understood that the order of steps or order for performing certain actions is immaterial so long as the present disclosure remains operable. Moreover, two or more steps or actions can be conducted simultaneously.

At various places in the present specification, features are disclosed in groups or in ranges. It is specifically intended that the description include each and every individual sub-combination of the members of such groups and ranges. For example, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20.

The use of any and all examples, or exemplary language herein, for example, "such as" or "including," is intended merely to illustrate better the present disclosure and does not pose a limitation on the scope of the disclosure unless claimed. No language in the specification should be construed as indicating any non-claimed element as essential to the practice of the present disclosure.

Various aspects of the disclosure are set forth herein under headings and/or in sections for clarity; however, it is understood that all aspects, embodiments, or features of the disclosure described in one particular section are not to be limited to that particular section but rather can apply to any aspect, embodiment, or feature of the present disclosure.

In some implementations, the present invention involves a specific binding event(s) that, advantageously, may result in a change in the composition and/or the shape of a dielectric arrangement of lamellar photonic material. Such change(s) may induce at least two exemplary observable colorimetric effects. First, a reflecting color change may occur due to a local refractive index change, for example, due to the presence of an analyte in a cavity of a first polymer (e.g., an MIP) and/or due to swelling of a first polymer layer due to the presence of the analyte in a cavity. More particularly, reflectivity may be selectively tuned to a desired wavelength(s) (e.g., within the visible spectrum and/or near infrared) by selectively modulating the optical thickness of a discrete layer of a polymeric phase due to swelling caused by binding of one or more specific analyte target molecules to the polymeric phase, which may change the photonic band gap and the reflected color. Second, a coordination complex of a specific analyte target molecule with a chromophore indicator (for example, incorporated into a polymer) may also result in a color change due to, for example, the intrinsic change of electronic state. Consequently, in some implementations, due to the second effect, the color change may be "amplified" so that an enhanced color contrast is seen upon the binding of one or more specific analyte target molecules to the chromophore of the polymeric phase. In some implementations, the color contrast may be increased or decreased as desired by tuning the interplay of the two colorimetric sensing mechanisms.

Device with Selectively Tunable Reflectivity

In certain embodiments, a colorimetric sensor of the invention is employed to detect an analyte of interest in a fluid sample. The sensor may include a lamellar photonic material having alternating layers of a first polymer layer and a second polymer layer. Each first polymer layer may be a molecularly imprinted polymer that defines a cavity shaped to receive an analyte of interest. The photonic material may be configured such that, when an analyte contacts the photonic material and becomes disposed within a cavity of the molecularly imprinted polymer, a refractive property of the photonic material changes, causing a detectable color change in the sensor. In various embodiments, the sensor (see, e.g., FIGS. 1A-1C) functions in a similar fashion to a Bragg reflector (or "Bragg mirror"). In other embodiments, the sensor (see, e.g., FIG. 1D) functions in a similar fashion to a diffraction grating.

Bragg diffraction, which results from the constructive interference of reflected light, occurs when reflected light passing through multiple layers of alternating materials remains in phase owing to the periodic distribution or periodicity of the spacing between the layering. For example, if the periodic distribution of the alternating layers is maintained at an integer multiple of the desired reflected wavelength ($\lambda$), then a device with a band gap that selectively reflects light of a particular wavelength can be formed. For example, within the visible spectrum, blue light has a wavelength of about 450-495 nm, and red light has a wavelength of about 620-750 nm. Thus, a device with a periodic distribution of about 450-495 nm reflects blue light, whereas a device with a periodic distribution of about 620-750 nm reflects red light.

As is known in the art, the periodic modulation of differing dielectric properties (e.g., refractive indices) between plural (e.g., two) alternating layers of materials may also be used to create photonic crystals to form a band gap to selectively reflect light of a particular wavelength. Periodic modulation may occur in one-dimensional (e.g., lamellar) structures, two-dimensional structures, or three-dimensional structures. For example, a lamellar distributed Bragg reflector (or Bragg mirror) may include a stack of film layers having alternating high refractive index ($n_1$) and low refractive index ($n_2$) materials, in which each film layer may have a thickness of a quarter wavelength ($\lambda/4$). As light passes from a lower refractive index layer into a higher refractive index material, the light reflected at the surface of the higher refractive index material undergoes a 180-degree phase shift; however, as light passes from a higher refractive index layer into a lower refractive index material, the reflected light at the surface of the lower refractive index material interferes constructively, increasing the intensity of the reflected light.

Figure 1A:
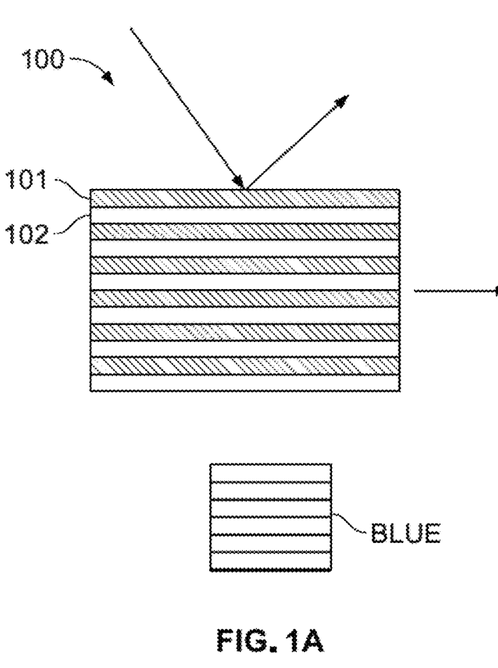
FIG. 1A schematically illustrates a colorimetric sensor reflecting a first color (e.g., blue) due to an initial local refractive index of a first polymer material in accordance with embodiments of the invention.
Figure 1B:
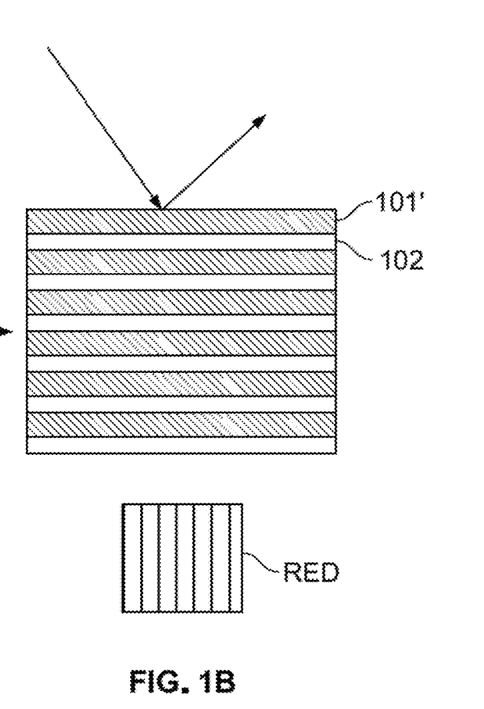
FIG. 1B schematically illustrates a colorimetric sensor reflecting a second, different color (e.g., red) due to a change in the local refractive index of the first polymer material of FIG. 1A caused by binding the analyte of interest.

An illustrative embodiment of a colorimetric chemical sensor with enhanced color sensitivity, which functions in a similar fashion to a Bragg reflector or Bragg mirror, is shown in FIGS. 1A and 1B. Advantageously, a sensor may be optically tuned to a selected wavelength (e.g., 450-495 nm) associated with a desired visible color (e.g., blue light) as a function of the reflectivity (or periodicity) of the lamellar photonic material making up the sensor and, more specifically, may enable users to selectively modulate the optical thickness of discrete sensor layers, e.g., via swelling (e.g., to about 620-750 nm) due to adherence or adsorption of an analyte target molecule(s) to the sensor. The adherence or adsorption and/or a swelling effect can change the photonic bandgap as well as the reflected color (e.g., to red light) that may be seen by the user.

FIG. 1A shows, for example, a sensor 100 in an original state that, due to the thicknesses of the first polymer layer 101 and the second polymer layer 102 and/or the refractive indices ($n_1$, $n_2$) of each of the polymer layers 101, 102, may appear as a first color at a shorter wavelength of the visible spectrum (e.g., blue). As shown in FIG. 1B, a volume and/or layer thickness change in the first polymer layer 101' due to swelling may modify the photonic band gap and the reflecting color of the material, which provides indicia of the presence of the analyte target molecule(s). In some implementations, the change in refractive index, for example, due to swelling, may appear or manifest as an optimized color toward the longer wavelengths of the visible spectrum (e.g., red).

In some variations, the sensors of the invention are one-dimensional photonic crystals. In general, there are two kinds of one-dimensional photonic crystal structures, each of which features a lamellar photonic material having alternating layers 101, 102 of (e.g., two or more) discrete polymeric phases. In a first embodiment depicted in FIG. 1C, the alternating layers 101, 102 are stacked on top of each other along the z-axis and upon a substrate 103, such that only a single bottom layer 102 makes direct contact with substrate 103. In this embodiment, the sensor 100 functions in a manner similar to a Bragg reflector or Bragg mirror, as described above. In contrast, in a second embodiment depicted in FIG. 1D, the alternating layers 101, 102 are disposed next to each other along the x-axis and upon the substrate 103, such that each alternating layer 101, 102 makes direct contact with substrate 103. In this embodiment, the sensor 100 functions in a similar fashion to a diffraction grating. As described further below, the substrate 103 can be adhered, or otherwise attached to, a surface of interest, for example, the surface of a cup or a straw.

Figure 1C:
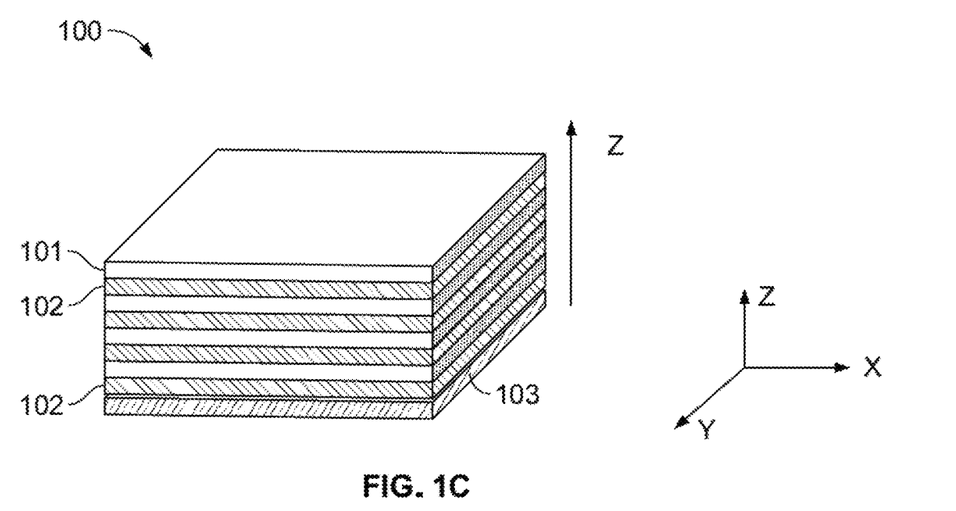
FIG. 1C schematically illustrates a photonic crystal which can act as a colorimetric sensor in accordance with embodiments of the invention.
Figure 1D:
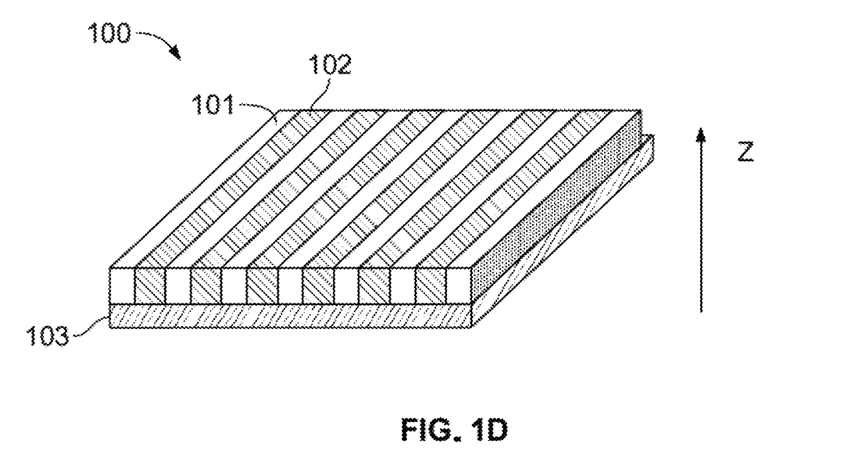
FIG. 1D schematically illustrates a photonic crystal which can act as a colorimetric sensor in accordance with embodiments of the invention.

In the embodiment depicted in FIG. 1D, sensor 100 includes a series of repeating layers 101, 102 that vary periodically in one dimension with two different refractive indices ($n_1$, $n_2$). In general, light incident on the grating surface is scattered into several "orders" of both transmitted and reflected waves. The diffraction orders exist at varying angles to the grating surface and are numbered such that the order which is equivalent to the reflected and transmitted wave from a smooth surface is the $0^{th}$ order, each subsequent order of a smaller or larger angle is given −1 and +1 numbers, respectively, and the order of each successive angle decrease or increase is respectively decremented (e.g., −2, −3, etc.) or incremented (e.g., +2, +3, etc.) appropriately.

Initially, in the absence of analyte target molecule(s) and at a given angle of observation, the diffraction grating reflects a selected wavelength (e.g., 450-495 nm) associated with a first visible color (e.g., blue light). When, however, the physical geometry of the diffraction grating is manipulated, e.g., via swelling of the polymer layer 101 in a vertical direction along the z-axis due to the adherence, binding or absorption of an analyte target molecule(s), the diffraction grating will, at the same given angle of observation, reflect a second, different wavelength (e.g., 620-750 nm) of the incident light, which leads to an observable color change in the sensor 100 (e.g., from blue to red).

The color reflected by a diffraction grating also depends, however, on the angle at which a user observes the diffraction grating. Because of this, sensor 100 depicted in FIG. 1D is, in one embodiment, employed in connection with a reference. The reference (not shown) may be the same as (e.g., identical to) the depicted sensor 100 and may be placed on the same plane as the depicted sensor 100 so that, in operation, the angle of observation is the same for both the depicted sensor 100 and the reference. The reference, however, may be covered with a transparent material, such as a plastic or glass, that is impervious to, and thus prevents the introduction of analyte into the reference. In this way, both the depicted sensor 100 and the reference reflect, in the absence of analyte, the same wavelength of the incident light and appear to be the same color, regardless of the angle at which a user observes the depicted sensor 100 and its reference. In the presence of analyte, however, the depicted sensor 100 and the reference appear as different colors, as the analytes will only have been adhered to, bound or absorbed by the depicted sensor 100.

In one embodiment, the sensors described herein are thin films. For example, in the embodiments depicted in FIGS. 1C and 1D, the thickness of the thin film along the z-axis may be on the micron scale (e.g., about 1 μm to about 1000 μm, about 10 μm to about 1000 μm, about 100 μm to about 1000 μm, about 1 μm to about 100 μm, about 1 μm to about 10 μm), while the lateral dimensions of the thin film along the x- and y-axes may on the centimeter scale (e.g., about 1 cm to about 1000 cm, about 10 cm to about 1000 cm, about 100 cm to about 1000 cm, about 1 cm to about 100 cm, about 1 cm to about 10 cm).

For the purpose of illustration and not limitation, illustrative embodiments of the invention are described for a sensor that functions in a similar fashion to a Bragg reflector or Bragg mirror and that, upon detecting an analyte of interest, transitions from reflecting an initial, blue light ($\lambda$=450-495 nm) to reflecting a red light ($\lambda$=620-750 nm) to provide an indication of the presence of the analyte of interest detectable by the unaided eye. Those of ordinary skill in the art can appreciate that sensors of the invention may use transitions from any spectral color having a first wavelength to another spectral color having a second, different wavelength.

Preferably, the first polymer layer and second polymer layer have a periodic distribution within the device such that, in a first state (i.e., as illustrated in FIG. 1A), a distance or height from the top of one first polymer layer to the top of any other first polymer layer is an integer multiple of the wavelength of the desired reflected color (e.g., 450p to 495p nm, where p is an integer). For example, the desired wavelength can be selected from wavelengths between about 1 nm to about 1000 nm, between about 100 nm to about 950 nm, between about 200 nm to about 900 nm, between about 300 nm to about 850 nm, and between about 400 nm to about 800 nm, which latter range covers the visible light spectrum. For exemplary embodiments using an initial, blue light, a periodic distribution between about 450 nm and about 495 nm may be appropriate.

In various embodiments, the first polymer layer is a hydrophilic polymer. A block co-polymer of a first polymer layer that is hydrophilic and a second polymer layer that is hydrophobic permits the first polymer domains and the second polymer domains to self-assemble into a structure (photonic material or sensor) having alternating first and second polymer layers as described herein.

The first polymer layer can include a chemical moiety (e.g., a "receptor" or "binding site") that can form a complex (e.g., host-guest chemistry) with an analyte target molecule of interest via a non-covalent bond, for example, via hydrogen bonding, metal coordination, hydrophobic forces, van der Waals forces, $\pi$-$\pi$ interactions, halogen bonding, and/or electrostatic and/or electromagnetic effects. The use of such a receptor can facilitate positioning of the analyte during creation a molecularly imprinted first polymer layer. Such a receptor can facilitate an analyte positioning itself in a cavity of the molecularly imprinted first polymer layer during use. Examples of such chemical moieties (receptors) include urea, thiourea, guanidine, aminopyridine, or amidine, cucurbituril, cyclodextrin, calixarene, crown ether, porphyrin, phthalocyanine, and the like. See, e.g., "Current developments in fluorescent PET (photoinduced electron transfer) sensors and switches," CHEM. SOC. REV. (2015), 44: 4203-4211; and Jonathan W. Steed, Jerry L. Atwood, Philip A. Gale, "Definition and Emergence of Supramolecular Chemistry," chapter in SUPRAMOLECULAR CHEMISTRY: FROM MOLECULES TO NANOMATERIALS (2012).

In various embodiments, for the purpose of selectively binding or disposing one or more analyte target molecules to or in the first polymer layer, the first polymer layer can include or can be a molecularly imprinted polymer (MIP) characterized by one or more cavities formed in the matrix of the first polymer layer, where the cavities have an affinity (e.g., physical and/or chemical) for an analyte of interest. MIPs are described in U.S. Pat. Nos. 8,241,575 and 9,285,352, the contents of which are incorporated by reference herein in their entirety for all purposes.

For example, a first polymer layer that is or includes a MIP may be formed by any molecular imprinting technique (e.g., a reversible addition-fragmentation chain transfer (RAFT) polymerization method, an atom-transfer radical polymerization (ATRP) method, a covalent bonding method, a self-assembly method, a hierarchical imprinting method, a polymerization packed bed method, or the like) that can leave a cavity in the first polymer layer, which cavity has an affinity to a chosen "analyte" molecule. In certain approaches, the process may involve initiating the polymerization of monomers in the presence of an analyte of interest that is then extracted leaving behind a cavity that is complementary in three-dimensional shape to, or a mirror image of, the three-dimensional surface of at least a portion of the analyte.

For example, the first polymer layer can include a monomer and a crosslinker, for example, a polymerizable monomer optionally with a receptor that can bind with an analyte molecule, such as urea or thiourea receptors, and a crosslinkable monomer that contains two or more reactive groups such a one vinyl moiety and one allylic moiety. Each of the two or more reactive groups should have different reactivities such that they can be employed in different stages of the manufacture of the first polymer layer. For example, a vinyl group can be employed for incorporation into a pre-polymer for the first polymer layer while the less reactive allylic functional group can be used as a crosslinker during the molecularly imprinting process. Other asymmetrically divinyl or vinyl/allyl or other monomer with two double bonds of different reactivity can be used, for example, methacrylate-based divinyl monomers such as hex-5-enyl methacrylate. See, e.g., "Controlled Divinyl Monomer Polymerization Mediated by Lewis Pairs: A Powerful Synthetic Strategy for Functional Polymers," ACS MACRO LETT. (2014), 3: 896-899 and "Branched polystyrene with abundant pendant vinyl functional groups from asymmetric divinyl monomer", JOURNAL OF POLYMER SCIENCE: PART A: POLYMER CHEMISTRY (2008), 46: 6023-6034.

The first polymer layer optionally can also include a chromophore. The chromophores include molecules that can form a complex with an analyte to induce a photoinduced electron transfer. For example, the first polymer layer can include a naphthalimide-containing molecularly imprinted polymer, for example, naphthalimide-based chromogenic molecules and/or their derivatives such as a 1,8-naphthalimide-containing polymer having a urea or thiourea moiety present (e.g., poly(urea-naphthalimide) or poly(thiourea-naphthalimide)). A chromophore can be used to enhance the color appearance and contrast. When a carboxylate ion is present, it forms a complex with urea or thiourea. The complex formation can change the electron density of the naphthalimide moiety leading to an optical absorption change. A suitable Bragg resonance can enhance such an optical change with a better saturation of the hue. For example, the color may be enhanced from a dull red to a very bright red so that a human observer can easily identify a color change, especially under diffuse illumination or low light conditions.

In various embodiments, a naphthalimide-based fluorescence indicator monomer can be integrated into the first polymer layer. The monomer can contain a urea binding site to respond to carboxylate-containing analytes that result in absorption and fluorescence change. Specific substitutions on the naphthalimide core may provide a binding partner for a carboxylate group present on an analyte of interest such as NaGHB. Furthermore, the naphthalimide can be functionalized with an alkene group so that it can be incorporated into a MIP. The binding of analyte can change the electron density in the naphthalimide aromatic ring and cause a change in the optical absorption properties. By combining the optical absorber (such as but not limiting to a chromophore) with structural color, the saturation of the color can be tuned so that it is more easily distinguished by the unaided eye.

Examples of chromophores can include xanthene derivatives: fluorescein, rhodamine, Oregon green, eosin, and Texas red; cyanine derivatives: cyanine, indocarbocyanine, oxacarbocyanine, thiacarbocyanine, and merocyanine; squaraine derivatives and ring-substituted squaraines, including Seta, SeTau, and Square dyes; naphthalene derivatives (including dansyl and prodan derivatives); coumarin derivatives; oxadiazole derivatives: pyridyloxazole, nitrobenzoxadiazole and benzoxadiazole; anthracene derivatives: anthraquinones, including DRAQ5, DRAQ7 and CyTRAK Orange; pyrene derivatives: cascade blue and the like; oxazine derivatives: Nile red, Nile blue, cresyl violet, and oxazine 170; acridine derivatives: proflavin, acridine orange, and acridine yellow; arylmethine derivatives: auramine, crystal violet, malachite green; tetrapyrrole derivatives: porphyrin, phthalocyanine, and bilirubin; and BODIPY dyes. See, e.g., "Current developments in fluorescent PET (photoinduced electron transfer) sensors and switches," CHEM. SOC. REV. (2015), 44: 4203-4211; "Fluorescent PET (Photoinduced Electron Transfer) sensors as potent analytical tools," ANALYST (2009), 134: 2385-2393; "Colorimetric "Naked Eye" Sensing of Anions in Aqueous Solution," J. ORG. CHEM. (2005), 70: 10875-10878, "Why, on Interaction of Urea-Based Receptors with Fluoride, Beautiful Colors Develop," J. ORG. CHEM. (2005), 70: 5717-5720; and "Colorimetric and fluorescent anion sensors: an overview of recent developments in the use of 1,8-naphthalimide-based chemosensors," CHEM. SOC. REV. (2010), 39: 3936-3953.

In certain embodiments, a first polymer layer can be formed from a cross-linkable monomer and a polymerizable monomer containing a polymerizable moiety, a receptor and a chromophore (e.g., poly(styrene-urea-naphthalimide)) as depicted in Scheme I below.

Scheme I

The result of RAFT polymerization of the reactants in Scheme I, i.e., the cross-linkable monomer and the polymerizable monomer, is a "pre-polymer" that includes a terminal RAFT agent. The pre-polymer typically is a soluble pre-polymer, which facilitates further creation of the first polymer layer.

Subsequently, as shown in Scheme II below, the pre-polymer can be combined with an analyte of interest ("analyte template") to perform the molecularly imprinting process thereby creating the cavities for the analyte. More specifically, the pre-polymer and analyte interact to associate the analytes with the urea receptors, which pre-polymer can be crosslinked to form the cavities after the analyte is removed from the MIP (e.g., by Soxlet extraction and/or solvent washing processes). As can be seen across the first row of Scheme II, the first polymer layer (MIP) is formed, which can include a RAFT agent at its terminal end. Advantageously, the functional groups of the RAFT agent, including a thiol group after reduction of the RAFT agent, can be used to secure the first polymer layer to a substrate such as in the top-down method of manufacturing discussed herein. The MIP at the end of this process also can be used to create a photonic material or sensor of the invention in a bottom-up layer-by-layer approach.

Scheme II

Scheme II also includes in its second row the formation of a block co-polymer of the MIP with polystyrene by polymerization, for example, by RAFT polymerization, with styrene. Such a block co-polymer then can self-assemble into the alternating layers first and second polymer layers of the photonic material or sensor.

Alternatively, as shown in Scheme III below, the prepolymer is reacted with styrene (which creates the second polymer layer) via RAFT polymerization to form a block co-polymer of the first polymer layer with the second polymer layer. The product of this reaction can be mixed with an analyte of interest to create a molecularly imprinted polymer (MIP) resulting in the block co-polymer of the MIP (first polymer layer) and hydrophobic second polymer layer that can be self-assembled into alternating layers of the first and second polymer layers.

Scheme III

With respect to the formation of the self-assembled structure of alternating first and second polymer layers, the block co-polymer can be dissolved in appropriate solvent (e.g., propylene glycol monomethyl ether acetate (5 wt %)) to make homogeneous solution. Then a small amount of co-polymer solution can be spin-cast onto a suitable substrate such as glass or glass-like substrates. The glass can have a surface treatment appropriate for the intended use, for example, a surface treated either with (3-aminopropyl)triethoxysilane or with (3-iodopropyl)trimethoxysilane, or a surface treated with a thin metallic film coating. The thickness of the metal film can be in the range of about 1 μm to about 1000 μm. One-dimensional lamellar structures can be formed via thermal annealing at low temperature (such as 50° C. for 24 hours) in a suitable vapor such as chloroform. See, e.g., "Broad-wavelength-range chemically tunable block-copolymer photonic gels," NATURE MATER. (2007), 6: 957-960.

Those of ordinary skill in the art can appreciate that each first polymer layer in a sensor of the invention may include any number of cavities appropriate to achieve the intended purpose. The number of cavities in a first polymer layer is, in part, determined by the dissociation constant of the material used for the first polymer layer. As different materials will have different dissociation constants, the number of cavities present in a first polymer layer will depend upon the type of material employed as the first polymer layer. In general, however, the average density of the cavities in a first polymer layer will be very high (e.g., up to $10^{10}$, $10^{15}$ or $10^{20}$ cavities per gram of first polymer). There may also be some variation in the number, density, and arrangement (e.g., distribution or pattern) of the cavities in the various first polymer layers, so long as each first polymer layer captures substantially the same number of analytes of interest and swells by substantially the same amount so as to create a color contrast with the sensor's original state in the absence of the analytes of interest.

Each formed cavity in the first polymer layer should have an affinity for a corresponding analyte of interest, which may include, for the purpose of illustration and not limitation, GBL, GHB, ketamine, Rohypnol, other pharmaceutical grade drugs, bacteria, allergens and proteins, 3-methyl-2-butene-1-thiol, substances that may be created during a process of creating 3-methyl-2-butene-1-thiol, substances that may be created when beer is exposed to sunlight, congeners (e.g., produced during fermentation and/or distillation of a beverage), and so forth.

In some embodiments, the second polymer layer is a hydrophobic polymer. A block co-polymer of a second polymer layer that is hydrophobic and a first polymer layer that is hydrophilic permits the first polymer domains and the second polymer domains to self-assemble into a structure (photonic material or sensor) having alternating first and second polymer layers as described herein.

The second polymer layer may be a polymer of the type that may be incorporated into, e.g., plastic cups, bottles (or other food/beverage/liquid containers), stirrers, straws, utensils, gloves, contraception devices, feminine hygiene products, and so forth. For example, materials for the second polymer layer may include polystyrene, substituted polystyrene, modified polystyrene, polyethylene, polypropylene, poly(vinyl chloride), and poly(vinylpyridine). A desired characteristic of material for a second polymer layer is that it does not change volume (e.g., swell) in the presence of the analyte of interest and/or the solvent/beverage being tested, or does not change volume in the presence of the analyte and/or the solvent/beverage being tested as much as the first polymer layer.

The second polymer layer may have a certain porosity that allows liquid to permeate through it to permit access to the internally-located surfaces including cavities and receptors, if present, of the first polymer layers in a self-assembled structure. The thickness of a thin film of such a structure is on the order of microns, such that a liquid should be able to diffuse through the alternating first and second polymer layers and/or to move via capillary action into the internal area of the alternating layers of the sensor.

In various embodiments of the invention, the affinity of a cavity for its corresponding analyte of interest causes a selective volume change in the first polymer layer when the analyte of interest adheres to, binds or is adsorbed or is disposed in a cavity of the MIP. For example, in the sensors depicted in FIGS. 1A-1C, the volume change typically results in a corresponding increase in height in the first polymer layer and in the periodic distribution between first and second polymer layers, which results in a visible change in color. For example, if the sensor initially has a periodic distribution of about 450-495 nm to reflect blue light, but a volume change causes the periodic distribution to be about 620-750 nm, then red light would be reflected and visible instead of blue light. Volume and height increases can be referred to as the "swelling" of the first polymer layer. In the self-assembly process, the amount of volume and/or height increase(s) of the first polymer layer can be controlled by adjusting the size distribution of the block co-polymer, for example, using the RAFT polymerization technique.

In certain embodiments, in addition to selectively tuning a sensor via swelling, the polymeric phases of the alternating layers of polymeric materials may be designed to affect particular wave propagation modes. For example, the polymeric materials of the polymer layers may be chosen so that, in the presence of a target analyte of interest, a periodic change of refractive index ($n_i$) in the various photonic materials occurs. Indeed, in some applications of the present invention, the mere presence of an analyte in a cavity in the first polymer layer can lead to a change in the refractive index ($n_1$) of the first polymer layers. Advantageously, such a change may result in a reflection of light of a selectively different wavelength.

In particular, whereas a swelling effect can enable users to optically tune a sensor using changes in the thickness or shape of the polymer layers within a sensor, molecular binding or disposition of an analyte in a cavity of the first polymer layer can enable users to optically tune the sensor using molecular changes affecting, for example, the index of refraction of the polymeric phase. More specifically, molecular binding may change the average refractive index according to the effective medium theory. For example, if $n_1$ is the refractive index of the polymeric material in the first polymer layers and $n_0$ is the refractive index of the air in the cavities in the absence of the analytes, then the average refractive index of the first polymer layers in the absence of the analytes depends upon the values of both $n_1$ and $n_0$. Once analytes having a refractive index of $n_2$, are received by the cavities, the average refractive index of the first polymer layers changes to instead depend upon the values of both $n_1$ and $n_2$. This change in the average refractive index of the first polymer layers causes a change in the color of the light reflected from the sensor.

Figure 2:
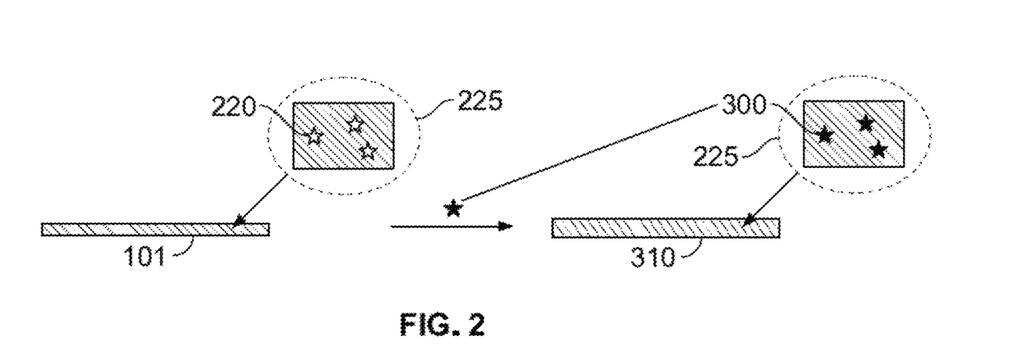
FIG. 2 schematically illustrates a molecularly imprinted polymer (MIP; 225) in a first polymer layer of a colorimetric sensor capturing target analyte molecules (300) in accordance with embodiments of the invention.

In FIG. 2, an exemplary MIP 225 with a chromophore indicator incorporated into a polymeric phase of a first polymer layer 101 is depicted. As previously described, in some implementations, a cavity(ies) 220 may be formed in a MIP 225, e.g., after the analyte molecule template is removed. Once a fluid containing an analyte of interest 300 is introduced to the first polymer layer 101 and MIP 225, the presence of and re-binding of any target analyte 300 in any of the cavities 220 of the MIP 225 may transform the first polymer layer 101 into a hybrid layer 310 having, for example, modified chemico-electric properties. This transformation may be accompanied by one or more of an increase in volume/height of the hybrid layer 310 and/or a production of a different composition in the hybrid layer 310, which may, for example, modify the local refractive index.

Methods of Manufacture

The colorimetric chemical sensor described herein may be manufactured in a variety of manners. For example, the periodic lamellar structure may be formed from self-assembly, microfabrication, or other appropriate methods. Exemplary bottom-up and top-down methods of manufacture are described below.

Bottom-Up Methods of Manufacture

Figure 3A:
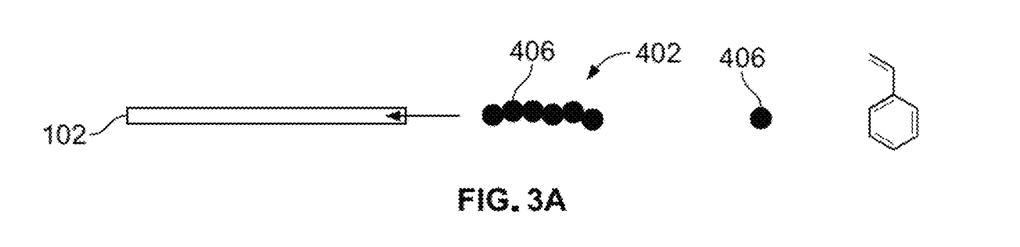
FIGS. 3A and 3B schematically illustrate a first bottom-up method of manufacturing a colorimetric sensor for detecting an analyte of interest in a fluid sample in accordance with embodiments of the invention.
Figure 3B:
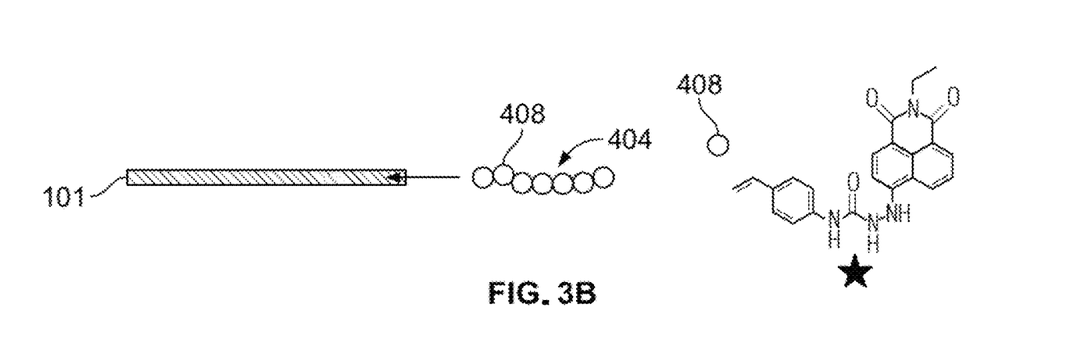

Referring to FIGS. 3A and 3B, an exemplary bottom-up method to produce each polymer layer of a lamellar photonic material is shown. In some implementations, a co-polymer may be synthesized as described herein to facilitate the microphase separation for self-assembly. For example, a second polymer layer 102 can include polystyrene 402, formed from styrene monomers 406. A first polymer layer 101 may be formed, with a chromophore indicator 408 as a co-polymer, for example, poly(urea-naphthalimide-styrene) (PUNS) polymer 404.

Figure 4:
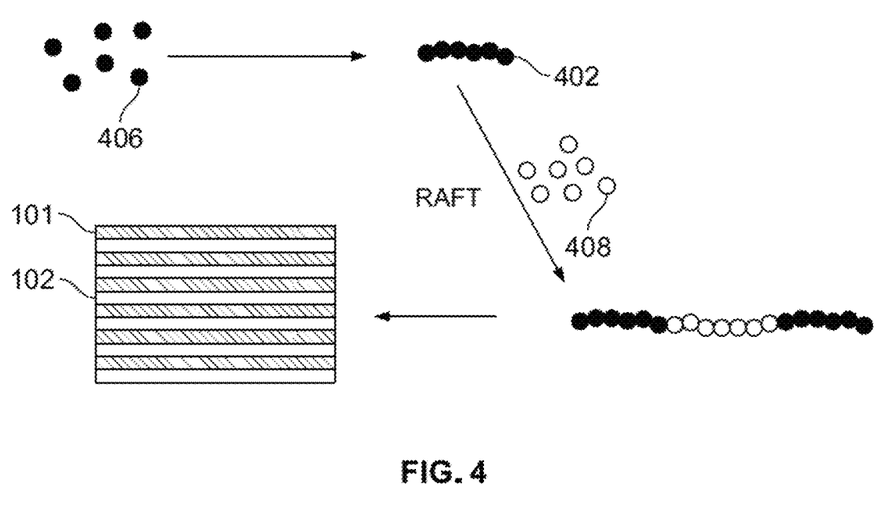
FIG. 4 schematically illustrates second bottom-up method of manufacturing a colorimetric sensor for detecting an analyte of interest in a fluid sample in accordance with embodiments of the invention.

Referring to FIG. 4, an exemplary polymerization synthesis route to form a self-assembled photonic material is depicted. The first and second layers are self-assembled into a one-dimensional structure rather than a three-dimensional cube. The self-assembly is accomplished due to the hydrophilic nature of the first polymer layer and the hydrophobic nature of the second polymer layer. For example, the block co-polymer in suitable solvent (e.g., propylene glycol methyl ether acetate (PGMEA)) can be spin-coated onto a suitable substrate such as glass.

In some implementations, as depicted, a block co-polymer of, e.g., polystyrene (first polymer layer) and poly(urea-naphthalimide-styrene) (second polymer layer) may be synthesized via, e.g., reversible addition-fragmentation chain transfer (RAFT) polymerization. Subsequent to the formation of the block co-polymer, it can self-assemble into the photonic material. Other polymerization methods, including but not limit to, atom-transfer radical polymerization (ATRP), may be used to control the molecular weight and distribution, as can RAFT polymerization.

Such a structure can also be produced by layer-by-layer assembly, for example, via spin-coating or dip-coating of each of the respective layers to form the alternating first polymer and second polymer layers. For example, the first polymer layer can be made from a pre-polymer without styrene blocks. The second polymer layer can be liquid polystyrene. Each of these polymers can be dissolved in appropriate solvent (e.g., water, ethanol, and/or propylene glycol monomethyl ether acetate) in suitable concentrations. Each of the polymers in the solvents then can be alternatingly spin-coated or dip-coated on to a selected substrate to form the final structure. Finally, the photonic material or sensor can be removed from the substrate, for example, by peeling, if the substrate is not the intended end use product. See, e.g., "Layer-by-Layer Assembly of Light-Responsive Polymeric Multilayer Systems," ADV. FUNCT. MATER. (2014), 24: 5624-5648.

Top-Down Method of Manufacture

Referring to FIGS. 5A through 5D, an exemplary embodiment of a top-down fabrication technique for forming a lamellar, colorimetric sensor that is capable of detecting an analyte of interest in a fluid sample is shown. In particular, FIGS. 5A through 5D illustrate a technique for forming a diffraction grating sensor of the type depicted in FIG. 1D. In some implementations, in a first step (FIG. 5A), a first polymer layer (e.g., poly(urea-naphthalimide) MIPs, or poly (thiourea-naphthalimide) MIPs, or the like) is placed on a polydimethylsiloxane (PDMS) stamp 500, a silicon mold, or the like. In some embodiments, the first polymer is a soluble polymer (e.g., a soluble MIP polymer including a chromophore) that is dissolved in a suitable solvent and then coated on the stamp 500 (or mold) via, for example, a spin coating process or a dip-coating process.

Figure 5A:
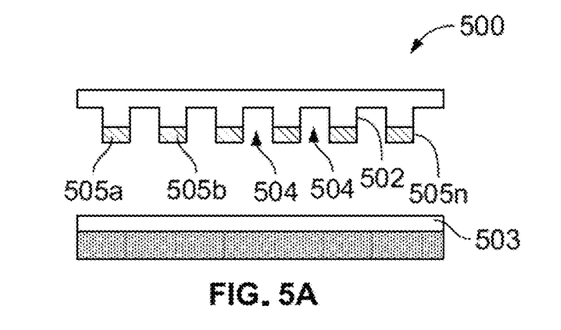
FIGS. 5A-5D schematically illustrate a top-down method of manufacturing a colorimetric sensor for detecting an analyte of interest in a fluid sample in accordance with embodiments of the invention.
Figure 5B:
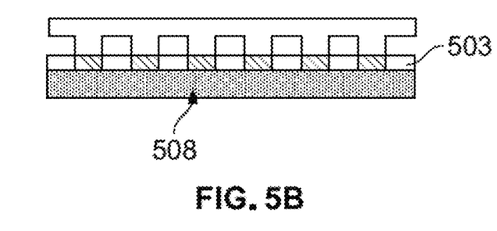

In some variations, the stamp 500 (or mold) includes a plurality of teeth 502 that are spaced 504 apart to provide a desired periodic distribution between adjacent first polymeric phases 505a, 505b . . . 505n of predefined dimension, thereby creating spaced apart first polymer layers. As previously described, each of the first polymer layers 505a, 505b . . . 505n can include or can be a molecularly imprinted polymer having one or more cavities that are adapted to receive an analyte of interest.

In various embodiments, the stamp is made from a uniform mold via a standard semiconductor process so that the uniformity among and between the teeth can be well controlled. For example, the stamp 500 may be made via a dry etching process, a wet etching process, or an e-beam lithography process. Having a uniform area on each tooth of the stamp and uniform spacing between each tooth allows one to place a uniform amount of the first polymer on each tooth and for the first polymer layers to be periodically spaced, which aids in ensuring that the above-described volume changes in each first polymer layer are substantially the same.

In some implementations, so that the stamp (or mold) may be more easily released from the co-polymer surface after an imprinting step, a thin release medium/molecule layer may be coated on the stamp (or mold), for example, on the surfaces of its teeth, prior to placing the first polymer on the stamp (or mold). Exemplary release media, for the purpose of illustration and not limitation, include a hydrophobic monolayer molecular coating, a fluorinated self-assembled monolayer, and a fluorinated diamond-like carbon coating.

Figure 5C:
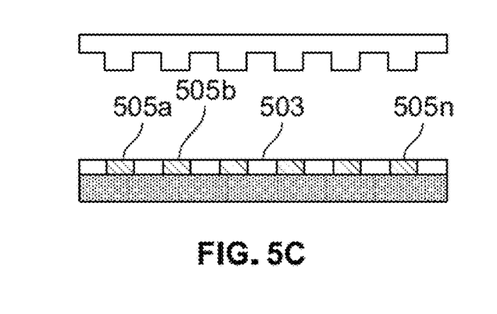
Figure 5D:
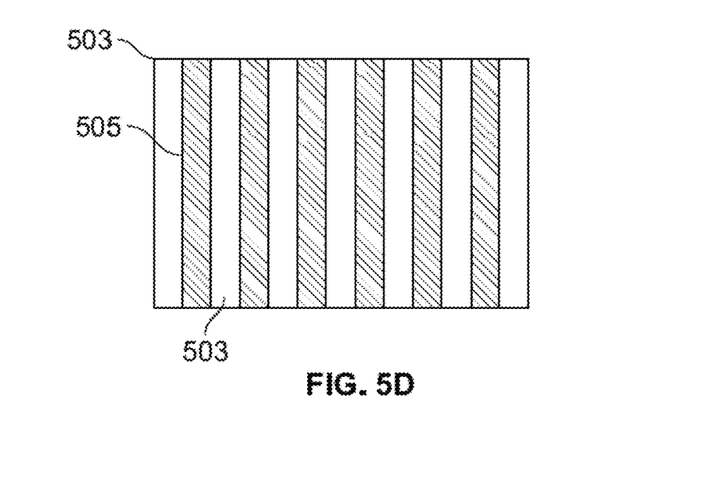

In a second step (FIG. 5B), the stamp 500 prints, imprints, transfers, or the like the first polymer layers 505a . . . 505n onto a second polymer layer 503 located on or coated on a glass surface/substrate 508. In one embodiment, the second polymer layer 503 is a UV-curable polymer, for example, a liquid polystyrene, and it is coated on the substrate 508 as a uniform thin film. In a final step (FIG. 5C), the stamp 500 is withdrawn, releasing and leaving the first polymer layers 505a . . . 505n in the second polymer layer 503. The second polymer can be in a liquid state such as a liquid polystyrene or liquid functionalized polystyrene. A liquid second polymer layer can be displaced by the first polymer layer on the teeth of the mold. Before removal of the mold as shown in FIG. 5C, a liquid second polymer layer can be solidified, for example, by ultraviolet (UV) curing or thermal treatment.

In certain embodiments, also prior to removal or after removal of the mold, the first polymer layer can be adhered to or bonded to the substrate, for example, covalently bonded to the substrate via thiol terminal groups of the first polymer layer (which can be present after the reduction of the RAFT agent. In particular embodiments, such attachment of bottom-up manufactured sensors can be realized to various substrates.

In certain embodiments, thiol groups can be reacted with silane coupling agents such as chlorosilane so that the first and/or second polymer layer can be covalently bonded to a glass surface. Alternatively, a glass surface may be functionalized with a silane coupling agent, for example, 3-(trimethoxysilyl)propylmethacrylate, then a thiol-ene click reaction can be employed to covalently bond the thiol terminal groups to the substrate. See, e.g., "Thiol-ene 'click' reactions and recent applications in polymer and materials synthesis," POLYM. CHEM. (2010), 1: 17-36; and "Thiol-ene 'click' reactions and recent applications in polymer and materials synthesis: A first update," POLYM. CHEM. (2014), 5: 4820-4870.

For non-glass surfaces such as other polymers, for example, plastics, surface treatment can include using oxygen plasma to activate the surface and generate sufficient hydroxyl (—OH) groups. A suitable silane coupling agent (e.g., 3-(trimethoxysilyl)propylmethacrylate) can be applied to the treated surface to produce a functionalized surface with terminal vinyl groups, which can react with thiol groups via a thiol-ene reaction as described herein. Physical binding such as thermal annealing also can be used to fuse the polymer layers to a substrate.

In particular embodiments, if a sensor is pre-formed on glass, flexible glass or other substrate, then the glass, flexible glass or other substrate can be bonded or otherwise adhered to glass drinkware using appropriate silane coupling agents, for example, as described herein.

In some embodiments, an option for adhering the polymer layers to a substrate can include introducing amine groups to substrate via silane chemistry, for example, using (3-aminopropyl)triethoxysilane (APTES) to generate a functionalized surface with terminal amine groups, which can act as anchors to immobilize the polymer layers.

The above-described micro-imprinting technique may produce a periodic photonic material having alternating layers of first and second polymers (FIG. 5D), similar to the self-assembled photonic materials described above, after the stamp (or mold) is released.

In some implementations, both the self-assembled and fabricated photonic structures combine the exemplary and non-limiting benefits of the color changes that can result from structural changes in the photonic materials with the color enhancing capability of the MIP chromophore, for example, upon binding with analyte target molecules.

In certain embodiments, the sensor of the invention is made separately from a manufacturing process for the drinkware (e.g., cup, glass, straw, stirrer, etc.). Once the sensor is made (e.g., using any of the manufacturing techniques described above), it can be bonded or otherwise adhered to the drinkware through, for example, a thermal adhesion process, covalent bonding, or a laser fusing process.

In some embodiments, the presence of the RAFT agent at the terminal end of the polymer chains can permit bonding to the surface of the drinkware object.

Practice of the invention will be more fully understood from the following example, which is presented herein for illustrative purposes only, and should not be construed as limiting the invention in any way.

Example

Figure 6:
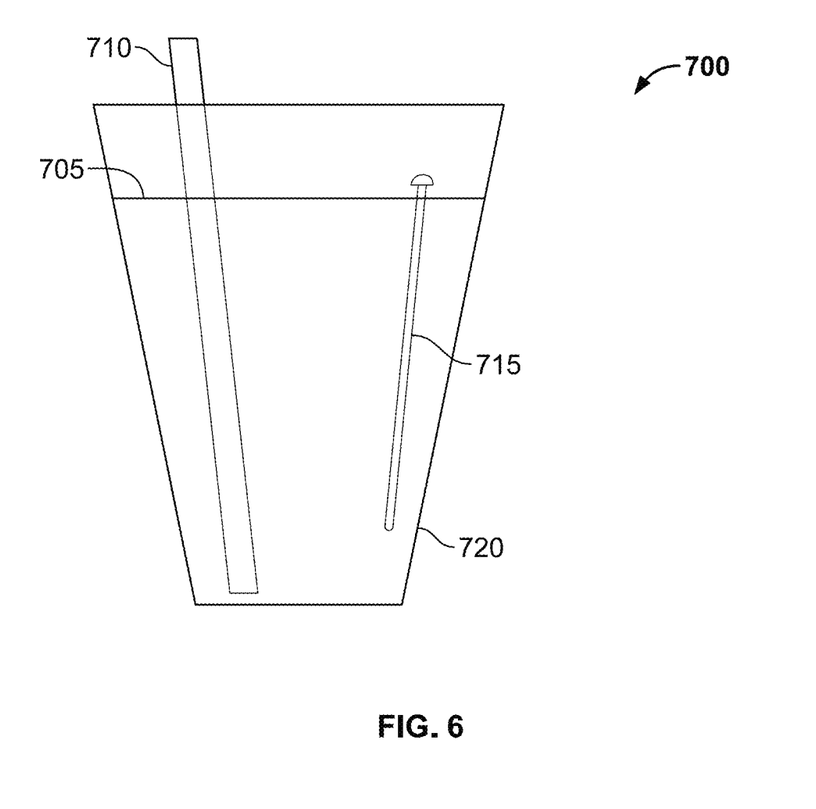
FIG. 6 schematically illustrates exemplary substrates for use in combination with colorimetric sensors for detecting an analyte of interest in a fluid sample in accordance with various embodiments of the invention.

In various embodiments, for example referring to FIG. 6, the colorimetric sensor described herein with reference to FIGS. 1A-1C, and prepared, for example, by the reaction schemes set forth in Schemes 1 and 2 or 3 described hereinabove, is disposed (e.g., as a thin film) upon or integrated within a surface of a substrate 700. In its normal or customary means of use, the substrate 700, the surface thereof, and the sensor disposed upon or integrated within that surface are exposed to a liquid 705 in which an analyte of interest may or may not be present. For the purpose of illustration and not limitation, exemplary substrates 700 include a straw 710, a swizzle stick or stirrer 715, a fluid receptacle 720 (e.g., a cup, a glass, and the like), and so forth.

In a first step, a fluid sample to be interrogated, e.g., a beverage, is brought into contact with the sensor. This may occur, for example, by pouring the beverage into a fluid receptacle into which the sensor has been integrated; by inserting a straw, stirrer, or swizzle stick into which the sensor has been integrated into the beverage; and so forth. In some applications, visual indicia of the sensor after initial contact with the beverage may provide a neutral or "safe" reading, e.g., the sensor may reflect blue light. If an analyte of interest is introduced into the beverage, a color change in the sensor, e.g., from blue to red, indicates that analyte is present in the fluid sample. Thus, in a second step, the sensor produces a color change when it comes into contact with the beverage. Advantageously, the sensor may be able to detect the presence of an analyte of interest for an extended period of time, such that a single sensor may be used to continue to detect for hours whether or not an analyte of interest is present in the beverage.

INCORPORATION BY REFERENCE

The entire disclosures of each of the patent documents and scientific articles cited herein are incorporated by reference herein in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A colorimetric sensor for detecting an analyte of interest in a fluid sample, the sensor comprising:
    a photonic material comprising alternating layers of a first polymer layer and a second polymer layer, the first polymer layer being a molecularly imprinted polymer defining a cavity shaped to receive an analyte, wherein the photonic material is configured such that, when the analyte contacts the photonic material and becomes disposed within the cavity of the molecularly imprinted polymer, a refractive property of the photonic material changes thereby to cause a detectable color change in the colorimetric sensor,
    wherein the first polymer layer comprises a chromophore indicator such that, when the cavity receives the analyte, the analyte causes a color change of the chromophore indicator and
    wherein the chromophore indicator comprises a naphthalimide moiety.

2. The colorimetric sensor of claim 1, wherein the chromophore indicator is incorporated into the first polymer layer as a co-polymer.

3. The colorimetric sensor of claim 1, wherein the first polymer layer is adapted such that, when the cavity receives the analyte, a thickness of the first polymer layer changes relative to a thickness of the second polymer layer, thereby changing the refractive property of the photonic material.

4. The colorimetric sensor of claim 1, wherein the alternating layers of the first polymer layer and the second polymer layer have a periodic distribution.

5. The colorimetric sensor of claim 4, wherein, in an absence of the analyte, a period of the periodic distribution is from about 1 nm to about 1000 nm, or from about 100 nm to about 950 nm, or from about 200 nm to about 900 nm, or from about 300 nm to about 850 nm, or from about 400 nm to about 800 nm.

6. The colorimetric sensor of claim 1, wherein the first polymer layer comprises poly(urea-naphthalimide), poly(thiourea-naphthalimide), poly(styrene-urea-naphthalimide) or poly(styrene-thiourea-naphthalimide).

7. The colorimetric sensor of claim 1, wherein the second polymer layer comprises polystyrene.

8. The colorimetric sensor of claim 1, wherein the photonic material is a photonic gel or a photonic crystal.

9. The colorimetric sensor of claim 1, wherein the sensor is disposed upon or integrated within a surface of a fluid receptacle, a stirrer, or a straw.

10. The colorimetric sensor of claim 1, wherein the analyte is selected from the group consisting of gamma-butyrolactone (GBL), gamma-hydroxybutyrate (GHB), ketamine, Rohypnol, pharmaceutical grade drugs, bacteria, allergens and proteins, 3-methyl-2-butene-1-thiol, substances that are created during a process of creating 3-methyl-2-butene-1-thiol, substances that are created when beer is exposed to sunlight, and congeners.

11. A method for detecting an analyte of interest in a fluid sample, the method comprising:
    contacting the colorimetric sensor of claim 1 with the fluid sample, and detecting whether the detectable color change occurs when the colorimetric sensor is contacted with the fluid sample, wherein the detectable color change is indicative that the analyte is present in the fluid sample.

12. The method of claim 11, wherein the chromophore indicator is incorporated into the first polymer layer as a co-polymer.

13. The method of claim 11, wherein the first polymer layer is adapted such that, when the cavity receives the analyte, a thickness of the first polymer layer changes relative to a thickness of the second polymer layer, thereby changing the refractive property of the photonic material.

14. The method of claim 11, wherein the alternating layers of the first polymer layer and the second polymer layer have a periodic distribution.

15. The method of claim 14, wherein, in the absence of the analyte, a period of the periodic distribution is from about 1 nm to about 1000 nm, or from about 100 nm to about 950 nm, or from about 200 nm to about 900 nm, or from about 300 nm to about 850 nm, or from about 400 nm to about 800 nm.

16. The method of claim 11, wherein the first polymer layer comprises poly(urea-naphthalimide), poly(thiourea-naphthalimide), poly(styrene-urea-naphthalimide) or poly(styrene-thiourea-naphthalimide).

17. The method of claim 11, wherein the second polymer layer comprises polystyrene.

18. The method of claim 11, wherein the photonic material is a photonic gel or a photonic crystal.

19. The method of claim 11, wherein the sensor is disposed upon or integrated within a surface of a fluid receptacle, a stirrer, or a straw.

20. The method of claim 11, wherein the analyte is selected from the group consisting of gamma-butyrolactone (GBL), gamma-hydroxybutyrate (GHB), ketamine, Rohypnol, pharmaceutical grade drugs, bacteria, allergens and proteins, 3-methyl-2-butene-1-thiol, substances that are created during a process of creating 3-methyl-2-butene-1-thiol, substances that are created when beer is exposed to sunlight, and congeners.

21. A method of manufacturing the colorimetric sensor of claim 1, the method comprising:
    creating a first set of spaced apart layers of a first polymer layer, wherein the first polymer layer is a molecularly imprinted polymer that defines a cavity shaped to receive an analyte of interest; and
    imprinting the first set of spaced apart layers into a second polymer layer thereby to create a photonic material comprising alternating layers of the first polymer layer and the second polymer layer configured such that, when the analyte contacts the photonic material and becomes disposed within the cavity of the molecularly imprinted polymer, a refractive property of the photonic material changes thereby to cause a detectable color change in the colorimetric sensor,
    wherein the first polymer layer comprises a chromophore indicator such that, when the cavity receives the analyte of interest, the analyte causes a color change of the chromophore indicator and
    wherein the chromophore indicator comprises a naphthalimide moiety.

22. The method of claim 21, wherein the chromophore indicator is incorporated into the first polymer layer as a co-polymer.

23. The method of claim 21, wherein the second polymer layer is disposed upon a surface of a substrate.

24. The method of claim 23, wherein the substrate is a fluid receptacle, a stirrer, or a straw.

25. The method of claim 23, wherein the first set of spaced apart layers is disposed upon a release medium.

26. The method of claim 25, wherein the release medium comprises at least one of a hydrophobic monolayer molecular coating, a fluorinated self-assembled monolayer, or a fluorinated diamond-like carbon coating.

27. The method of claim 21, wherein the first polymer layer comprises poly(urea-naphthalimide), poly(thiourea-naphthalimide), poly(styrene-urea-naphthalimide), or poly(styrene-thiourea-naphthalimide).

28. The method of claim 21, wherein the second polymer layer comprises polystyrene.

29. The method of claim 21, wherein the alternating layers of the first polymer layer and the second polymer layer have a periodic distribution.

30. The method of claim 21, wherein the analyte is selected from the group consisting of gamma-butyrolactone (GBL), gamma-hydroxybutyrate (GHB), ketamine, Rohypnol, pharmaceutical grade drugs, bacteria, allergens and proteins, 3-methyl-2-butene-1-thiol, substances that are created during a process of creating 3-methyl-2-butene-1-thiol, substances that are created when beer is exposed to sunlight, and congeners.

* * * * *